United States Patent
Faucher et al.

(10) Patent No.: US 8,652,723 B2
(45) Date of Patent: *Feb. 18, 2014

(54) TONER PARTICLES COMPRISING COLORANT-POLYESTERS

(75) Inventors: Santiago Faucher, Oakville (CA);
Kimberly D. Nosella, Mississauga (CA);
Shigang S. Qiu, Toronto (CA)

(73) Assignee: Xerox Corporation, Norwalk, CT (US)

(*) Notice: Subject to any disclaimer, the term of this patent is extended or adjusted under 35 U.S.C. 154(b) by 280 days.

This patent is subject to a terminal disclaimer.

(21) Appl. No.: 13/043,838

(22) Filed: Mar. 9, 2011

(65) Prior Publication Data

US 2012/0231386 A1 Sep. 13, 2012

(51) Int. Cl.
*G03G 9/00* (2006.01)

(52) U.S. Cl.
USPC ............ 430/108.4; 430/108.1; 430/109.1; 430/109.4; 430/137.14

(58) Field of Classification Search
USPC ........ 430/108.1, 108.4, 109.1, 109.4, 137.14
See application file for complete search history.

(56) References Cited

U.S. PATENT DOCUMENTS

| | | | |
|---|---|---|---|
| 3,590,000 A | 6/1971 | Palermiti et al. | |
| 3,800,588 A | 4/1974 | Larson et al. | |
| 4,284,729 A | 8/1981 | Cross et al. | |
| 4,298,672 A | 11/1981 | Lu | |
| 4,338,390 A | 7/1982 | Lu | |
| 4,702,574 A | 10/1987 | Bawa | |
| 5,231,135 A | 7/1993 | Machell et al. | |
| 5,278,020 A | 1/1994 | Grushkin et al. | |
| 5,290,654 A | 3/1994 | Sacripante et al. | |
| 5,302,486 A | 4/1994 | Patel et al. | |
| 5,308,734 A | 5/1994 | Sacripante et al. | |
| 5,344,738 A | 9/1994 | Kmiecik-Lawrynowicz et al. | |
| 5,346,797 A | 9/1994 | Kmiecik-Lawrynowicz et al. | |
| 5,348,832 A | 9/1994 | Sacripante et al. | |
| 5,364,729 A | 11/1994 | Kmiecik-Lawrynowicz et al. | |
| 5,366,841 A | 11/1994 | Patel et al. | |
| 5,370,963 A | 12/1994 | Patel et al. | |
| 5,403,693 A | 4/1995 | Patel et al. | |
| 5,405,728 A | 4/1995 | Hopper et al. | |
| 5,418,108 A | 5/1995 | Kmiecik-Lawrynowicz et al. | |
| 5,496,676 A | 3/1996 | Croucher et al. | |
| 5,501,935 A | 3/1996 | Patel et al. | |
| 5,527,658 A | 6/1996 | Hopper et al. | |
| 5,585,215 A | 12/1996 | Ong et al. | |
| 5,621,022 A | 4/1997 | Jaeger et al. | |
| 5,650,255 A | 7/1997 | Ng et al. | |
| 5,650,256 A | 7/1997 | Veregin et al. | |
| 5,723,253 A | 3/1998 | Higashino et al. | |
| 5,744,520 A | 4/1998 | Kmiecik-Lawrynowicz et al. | |
| 5,747,215 A | 5/1998 | Ong et al. | |
| 5,763,133 A | 6/1998 | Ong et al. | |
| 5,766,818 A | 6/1998 | Smith et al. | |
| 5,804,349 A | 9/1998 | Ong et al. | |
| 5,827,633 A | 10/1998 | Ong et al. | |
| 5,840,462 A | 11/1998 | Foucher et al. | |
| 5,853,944 A | 12/1998 | Foucher et al. | |
| 5,869,215 A | 2/1999 | Ong et al. | |
| 5,916,725 A | 6/1999 | Patel et al. | |
| 6,001,524 A * | 12/1999 | Yoon et al. ............ | 430/109.4 |
| 6,120,967 A | 9/2000 | Hopper et al. | |
| 6,214,507 B1 | 4/2001 | Sokol et al. | |
| 6,221,137 B1 | 4/2001 | King et al. | |
| 6,472,523 B1 | 10/2002 | Banning et al. | |
| 6,476,219 B1 | 11/2002 | Duff et al. | |
| 6,547,380 B2 | 4/2003 | Smith et al. | |
| 6,576,747 B1 | 6/2003 | Carlini et al. | |
| 6,576,748 B1 | 6/2003 | Carlini et al. | |
| 6,590,082 B1 | 7/2003 | Banning et al. | |
| 6,646,111 B1 | 11/2003 | Carlini et al. | |
| 6,663,703 B1 | 12/2003 | Wu et al. | |
| 6,673,139 B1 | 1/2004 | Wu et al. | |
| 6,696,552 B2 | 2/2004 | Mayo et al. | |
| 6,713,614 B2 | 3/2004 | Carlini et al. | |
| 6,726,755 B2 | 4/2004 | Titterington et al. | |
| 6,755,902 B2 | 6/2004 | Banning et al. | |
| 6,821,327 B2 | 11/2004 | Jaeger et al. | |
| 6,958,406 B2 | 10/2005 | Banning et al. | |
| 7,053,227 B2 | 5/2006 | Jaeger et al. | |
| 7,381,831 B1 | 6/2008 | Banning et al. | |
| 7,427,323 B1 | 9/2008 | Birau et al. | |
| 2004/0024151 A1 | 2/2004 | Becker et al. | |
| 2006/0022176 A1* | 2/2006 | Wang et al. ............ | 252/583 |

(Continued)

FOREIGN PATENT DOCUMENTS

| | | |
|---|---|---|
| EP | 2 116 608 A2 | 11/2009 |
| JP | A-59155418 | 9/1984 |
| JP | A-63317526 | 12/1988 |

OTHER PUBLICATIONS

Luo et al. (Cellular Internalization of Poly(ethylene oxide)-b-poly(E-caprolactone) Diblock Copolymer Micelles, Bioconjugate Chem. 2002, 13, 1259-1265).*
U.S. Appl. No. 12/879,587, filed Sep. 10, 2010, by Faucher et al.
U.S. Appl. No. 12/879,587, filed Sep. 10, 2010.
Sep. 21, 2012 Office Action issued in U.S. Appl. No. 12/879,587.
Dec. 11, 2012 Office Action issued in U.S. Appl. No. 12/879,587.
Apr. 3, 2012 Office Action issued in U.S. Appl. No. 12/938,737.
Jan. 6, 2012 Search Report issued in British Application No. GB 1115521.5.
Takwa et al., "Single-Step, Solvent-Free Enzymatic Route to #, #-Functionalized Polypentadecalatone Macromonomers," Macromolecules, Jun. 26, 2008, pp. 5230-5236, vol. 41, No. 14.
Varma et al., "Enzyme Catalyzed Synthesis of Polyesters," Progress in Polymer Science, Aug. 10, 2005, pp. 949-981, vol. 30.

(Continued)

*Primary Examiner* — Stewart Fraser
(74) *Attorney, Agent, or Firm* — Oliff & Berridge, PLC

(57) ABSTRACT

A toner composition including a colorant-polyester polymer having at least one colorant and at least one polyester resin, an optional non-colorant polyester polymer, an optional additional colorant, an optional wax, and an optional additive, where the colorant is covalently linked to some or all of the polyester resin and the polyester resin is obtained by polymerizing a lactone using an enzyme catalyst. Methods for preparing a toner composition including an emulsion aggregation process.

17 Claims, No Drawings

(56) References Cited

U.S. PATENT DOCUMENTS

| | | |
|---|---|---|
| 2009/0092918 A1 | 4/2009 | Moffat |
| 2009/0220880 A1 | 9/2009 | Moffat et al. |
| 2009/0280429 A1* | 11/2009 | Farrugia et al. .......... 430/137.15 |
| 2010/0055750 A1* | 3/2010 | Wosnick ....................... 435/135 |
| 2010/0081076 A1 | 4/2010 | Wosnick et al. |
| 2012/0065359 A1* | 3/2012 | Faucher et al. ............... 528/354 |

OTHER PUBLICATIONS

Webster's Third New Dictionary, Unabridged, Literature Online Reference Edition, copyright 1993, definition for "dye."

Albertsson et al (Recent developments in enzyme-catalyzed ring-opening polymerization, Advanced Drug Delivery Reviews 60 (2008) pp. 1077-1093.

Luo et al. (Cellular Internalization of Polyethylene oxide)-b-poly(E-caprolactone) Diblock Copolymer Micelles, Bioconjugate Chem. 2002, 13, pp. 1259-1265.

Van der Meulen et al. (Polymers from Functional Macrolactones as Potential Biomaterials: Enzymatic Ring Opening Polymerization, Biodegradation, and Biomacromolecules 2008, 9, pp. 3404-3410.

* cited by examiner

TONER PARTICLES COMPRISING COLORANT-POLYESTERS

TECHNICAL FIELD

The present disclosure generally relates to toner particles comprising colorant-polyesters and methods for producing such toner compositions using the emulsion aggregation process.

CROSS-REFERENCE TO RELATED APPLICATIONS

U.S. patent application Ser. No. 12/879,587, filed Sep. 10, 2010, the disclosure of which is hereby incorporated by reference in its entirety, describes a method of covalently linking colorants to polyesters using enzymatic polymerization and colorant-polyesters produced using the enzymatic polymerization.

BACKGROUND

Emulsion aggregation toners are excellent toners to use in forming print and/or xerographic images in that the toners may be made to have uniform sizes and in that the toners are environmentally friendly. U.S. patents describing emulsion aggregation toners include, for example, U.S. Pat. Nos. 5,370,963, 5,418,108, 5,290,654, 5,278,020, 5,308,734, 5,344,738, 5,403,693, 5,364,729, 5,346,797, 5,348,832, 5,405,728, 5,366,841, 5,496,676, 5,527,658, 5,585,215, 5,650,255, 5,650,256, 5,501,935, 5,723,253, 5,744,520, 5,763,133, 5,766,818, 5,747,215, 5,827,633, 5,853,944, 5,804,349, 5,840,462, and 5,869,215, all of which are incorporated herein by reference in their entirety.

Two main types of emulsion aggregation toners are known. First is an emulsion aggregation process that forms acrylate based, e.g., styrene acrylate, toner particles. See, for example, U.S. Pat. No. 6,120,967, incorporated herein by reference in its entirety, as one example of such a process. Second is an emulsion aggregation process that forms polyester, e.g., sodio sulfonated polyester toner particles. See, for example, U.S. Pat. No. 5,916,725, incorporated herein by reference in its entirety, as one example of such a process.

Fluorescent toners may be used as an authenticating feature in the document security industry. Secure documents, for example, documents that are difficult to forge, may be created using toners that include fluorescent agents either alone or in combination with ordinary pigments. Features printed using fluorescent toners are usually invisible under visible light, due to the colorless nature of the security inks or due to masking by other colorants in the document. Under ultraviolet illumination, however, the fluorescent features of the document are revealed in the form of a bright emission by the fluorescent dyes in the visible spectrum. For example, certain bank notes utilize visible features, such as holographic patches, microprinting and microtextures to conceal additional fluorescent threads and/or multi-colored emblems embedded in the bank note, which are only revealed under specific light frequencies. These features provide an increased level of security against counterfeiters by making the copying process of such a document more difficult. A fluorescent toner composition may also be used for digital imaging in tissues or other applications of interest as the fluorescence is easily detectable in the material that is to be imaged.

However, pigments are difficult to disperse into polymeric materials and gels on account of their lack of solubility, size, tendency to aggregate and physical property differences. A great deal of effort and time is spent dispersing pigments into aqueous dispersions using surface active agents (surfactants) which are detrimental to the performance of the parent particle in the final xerographic application. Ideally, the colorant used in emulsion aggregation should eliminate the need for this costly dispersion and eliminate the use of surfactants. Often dyes are used instead of pigments to overcome these shortfalls. However, dyes are expensive and so add cost to the final product. Dyes can furthermore affect the material's properties based on their loading and because of their low molecular weight lead to depressions of Tg and other such property modifications. These negative attributes all relate to the low molecular weight of the molecules in comparison to the gel or macromolecular matrix that holds them. In toners, this effect leads to a depression of the toner Tg along with the above-cited additional challenges. Ideally, the colorant used should therefore be derived from pigments, be compatible with the resin matrix and offer the above advantage of not necessitating dispersion processing. Finally, aggregation of the pigment in the final application can be another shortfall that leads to product (toner) failure. For highly pigmented toners this is particularly troublesome as it leads to high dielectric loss and therefore poor transfer of the toner to the page from the transfer belt. Ideally, this new colorant would also therefore be highly compatible with the resin such that it would not phase separate and produce a toner particle with a low dielectric loss.

Improved toners and methods for producing toners, which eliminates the need for pigment dispersions and high levels of surfactant, remain desirable. Such toners and processes may reduce production costs and effectively produce a particle with a homogenously distributed colorant.

SUMMARY

A toner composition of the present disclosure includes a colorant-polyester polymer comprising at least one colorant and at least one polyester resin, an optional non-colorant polyester, an optional additional colorant, an optional wax, and an optional additive, where the colorant is covalently linked to some or all of the polyester resin and the polyester resin is obtained by polymerizing a lactone using an enzyme catalyst.

A method for preparing a toner composition of the present disclosure includes forming a colorant-polyester resin emulsion comprising a colorant-polyester polymer an optional non-colorant polyester, mixing the colorant-polyester resin emulsion, an optional colorant, an optional wax, and an optional additive to form a mixture, and aggregating and coalescing the mixture to form the toner composition, where the colorant-polyester polymer comprises at least one colorant and at least one polyester resin, the colorant is covalently linked to some or all of the polyester resin and the polyester resin is obtained by polymerizing a lactone using an enzyme catalyst.

Another method for preparing a toner composition of the present disclosure includes providing a reaction solution comprising an ester monomer, a colorant having or functionalized to have at least one hydroxyl group, and an enzymatic catalyst; reacting the ester monomer and the colorant using the enzymatic catalyst to produce a polymeric product, where the polymeric product comprises a colorant-polyester polymer; separating the polymeric product from the reaction solution; forming a latex from the polymeric product; and using the resulting polymeric product emulsion in an emulsion aggregation process to produce a toner composition.

DETAILED DESCRIPTION OF EMBODIMENTS

The present disclosure provides toner compositions and processes for producing toner compositions. In embodiments, a toner composition of the present disclosure comprises a colorant-polyester polymer, the colorant-polyester polymer comprising at least one colorant and at least one polyester resin, where the colorant is covalently linked to some or all of the polyester resin and the polyester resin is obtained by polymerizing a lactone using an enzyme catalyst. In embodiments, the toner composition may be obtained by the emulsion aggregation process.

Colorant-Polyester Compounds

Reaction Solution

In embodiments, the colorant-polyester polymer may be produced by an enzymatic polymerization process, which is accomplished by providing a reaction solution that comprises a colorant, an ester monomer and an enzymatic catalyst. The enzymatic polymerization reaction may further comprise water. The polymerization may be initiated by either water present in the reaction medium or by the hydroxyl groups present on the colorant, or both. Thus, two polyester populations may be created through this mechanism in the absence of dry solvents and monomers: one polyester population has a colorant attached to it and the other polyester population has an α-hydroxyl group, with no colorant attached to it. The polyester with an α-hydroxyl group is not colored. By adjusting the amount of water and concentration of starting materials, the ratio of colored colorant-polyester to non-colored polyester can be changed.

Colorants

Suitable colorants may be dyes, or pigments, or mixtures of dye, or mixtures of pigments and dyes, and the like.

A colorant is reactive with an ester monomer present in the reaction solution via the enzyme catalyst. This may be achieved with a colorant having a reactive end group. An example of a reactive group of a colorant is a reactive hydroxyl group.

A colorant may also be functionalized to have a reactive end group to enable the colorant to be reactive with an ester monomer. This may be achieved by functionalizing the colorant to have a reactive end group.

Examples of suitable dyes include Neozapon Red 492 (BASF); Orasol Red G (Ciba); Direct Brilliant Pink B (Oriental Giant Dyes); Direct Red 3BL (Classic Dyestuffs); Supranol Brilliant Red 3BW (Bayer AG); Lemon Yellow 6G (United Chemie); Light Fast Yellow 3G (Shaanxi); Aizen Spilon Yellow C-GNH (Hodogaya Chemical); Bernachrome Yellow GD Sub (Classic Dyestuffs); Cartasol Brilliant Yellow 4GF (Clariant); Cibanon Yellow 2GN (Ciba); Orasol Black CN (Ciba); Savinyl Black RLSN(Clariant); Pyrazol Black BG (Clariant); Morfast Black 101 (Rohm & Haas); Diaazol Black RN (ICI); Orasol Blue GN (Ciba); Savinyl Blue GLS (Clariant); Luxol Fast Blue MBSN (Pylam Products); Sevron Blue 5GMF (Classic Dyestuffs); Basacid Blue 750 (BASF), Neozapon Black X51 (BASF); Classic Solvent Black 7 (Classic Dyestuffs); Sudan Blue 670 (C.I. 61554) (BASF); Sudan Yellow 146 (C.I. 12700) (BASF); Sudan Red 462 (C.I. 26050) (BASF); C.I. Disperse Yellow 238; Neptune Red Base NB543 (BASF, C.I. Solvent Red 49); Neopen Blue FF-4012 (BASF); Lampronol Black BR from ICI (C.I. Solvent Black 35); Morton Morplas Magenta 36 (C.I. Solvent Red 172); metal phthalocyanine colorants such as those disclosed in U.S. Pat. No. 6,221,137, the disclosure of which is totally incorporated herein by reference; and the like. Polymeric dyes can also be used, such as those disclosed in, for example, U.S. Pat. No. 5,621,022 and U.S. Pat. No. 5,231,135, the disclosures of each of which are entirely incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactant Orange X-38, uncut Reactant Blue X-17, Solvent Yellow 162, Acid Red 52, Solvent Blue 44, and uncut Reactant Violet X-80.

Examples of suitable pigments include PALIOGEN Violet 5100 (BASF); PALIOGEN Violet 5890 (BASF); HELIOGEN Green L8730 (BASF); LITHOL Scarlet D3700 (BASF); SUNFAST Blue 15:4 (Sun Chemical); Hostaperm Blue B2G-D (Clariant); Hostaperm Blue B4G (Clariant); Permanent Red P-F7RK; Hostaperm Violet BL (Clariant); LITHOL Scarlet 4440 (BASF); Bon Red C (Dominion Color Company); ORACET Pink RF (Ciba); PALIOGEN Red 3871 K (BASF); SUNFAST Blue 15:3 (Sun Chemical); PALIOGEN Red 3340 (BASF); SUNFAST Carbazole Violet 23 (Sun Chemical); LITHOL Fast Scarlet L4300 (BASF); SUNBRITE Yellow 17 (Sun Chemical); HELIOGEN Blue L6900, L7020 (BASF); SUNBRITE Yellow 74 (Sun Chemical); SPECTRA PAC C Orange 16 (Sun Chemical); HELIOGEN Blue K6902, K6910 (BASF); SUNFAST Magenta 122 (Sun Chemical); HELIOGEN Blue D6840, D7080 (BASF); Sudan Blue OS (BASF); NEOPEN Blue FF4012 (BASF); PV Fast Blue B2GO1 (Clariant); IRGALITE Blue BCA (Ciba); PALIOGEN Blue 6470 (BASF); Sudan Orange G (Aldrich); Sudan Orange 220 (BASF); PALIOGEN Orange 3040 (BASF); PALIOGEN Yellow 152, 1560 (BASF); LITHOL Fast Yellow 0991 K (BASF); PALIOTOL Yellow 1840 (BASF); NOVOPERM Yellow FGL (Clariant); Ink Jet Yellow 4G VP2532 (Clariant); Toner Yellow HG (Clariant); Lumogen Yellow D0790 (BASF); Suco-Yellow L1250 (BASF); Suco-Yellow D1355 (BASF); Suco Fast Yellow D1 355, D1 351 (BASF); HOSTAPERM Pink E 02 (Clariant); Hansa Brilliant Yellow 5GX03 (Clariant); Permanent Yellow GRL 02 (Clariant); Permanent Rubine L6B 05 (Clariant); FANAL Pink D4830 (BASF); CINQUASIA Magenta (DU PONT); PALIOGEN Black L0084 (BASF); Pigment Black K801 (BASF); and carbon blacks such as REGAL 330™ (Cabot), Nipex 150 (Degusssa) Carbon Black 5250 and Carbon Black 5750 (Columbia Chemical), and the like, as well as mixtures thereof.

Also suitable are the colorants disclosed in U.S. Pat. No. 6,472,523, U.S. Pat. No. 6,726,755, U.S. Pat. No. 6,476,219, U.S. Pat. No. 6,576,747, U.S. Pat. No. 6,713,614, U.S. Pat. No. 6,663,703, U.S. Pat. No. 6,755,902, U.S. Pat. No. 6,590,082, U.S. Pat. No. 6,696,552, U.S. Pat. No. 6,576,748, U.S. Pat. No. 6,646,111, U.S. Pat. No. 6,673,139, U.S. Pat. No. 6,958,406, U.S. Pat. No. 6,821,327, U.S. Pat. No. 7,053,227, U.S. Pat. No. 7,381,831 and U.S. Pat. No. 7,427,323, the disclosures of each of which are incorporated herein by reference in their entirety.

In embodiments, solvent dyes are employed. An example of a solvent dye suitable for use herein may include spirit soluble dyes. Examples of suitable spirit solvent dyes include Neozapon Red 492 (BASF); Orasol Red G (Ciba); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH (Hodogaya Chemical); Cartasol Brilliant Yellow 4GF (Clariant); Pergasol Yellow CGP (Ciba); Orasol Black RLP (Ciba); Savinyl Black RLS (Clariant); Morfast Black Conc. A (Rohm and Haas); Orasol Blue GN (Ciba); Savinyl Blue GLS (Sandoz); Luxol Fast Blue MBSN (Pylam); Sevron Blue 5GMF (Classic Dyestuffs); Basacid Blue 750 (BASF); Neozapon Black X51 [C.I. Solvent Black, C.I. 12195] (BASF); Sudan Blue 670 [C.I. 61554] (BASF); Sudan Yellow 146 [C.I. 12700] (BASF); Sudan Red 462 [C.I. 260501] (BASF); mixtures thereof and the like.

Fluorescent Colorant

The colorant may be a fluorescent colorant. Any fluorescent colorant that is capable of chemically attaching to a polyester during enzymatic polymerization may be used. In embodiments, the fluorescent colorants produced herein are essentially colorless, i.e., prints made with the fluorescent toners blended with the fluorescent colorants on suitable selected paper substrates are not visible under normal viewing conditions. However, these fluorescent colorants may become visible when exposed to light of a suitable wavelength, e.g., ultraviolet (UV) light of a predetermined wavelength. This visibility may be imparted to the toner by the addition of the fluorescent colorants, which may be a material that only becomes visible upon exposure to UV light. A fluorescent colorant may be an emitting component or a component that fluoresces when exposed to UV light of a wavelength of from about 10 nanometers to about 400 nanometers, such as from about 60 to about 350 nanometers, or from about 110 to about 300 nanometers of the UV spectral region.

In embodiments, suitable fluorescent colorants include 4,4'-bis(styryl)biphenyl, 2-(4-phenylstilben-4-yl)-6-butylbenzoxazole, 2-(2-hydroxyphenyl)benzothiazole, beta-methyl umbelliferone, 4-methyl-7-dimethylaminocoumarin, 4-methyl-7-aminocoumarin, N-methyl-4-methoxy-1,8-naphthalimide, 9,10-bis(phenethynyl) anthracene, 5,12-bis(phenethynyl)naphthacene, DAYGLO INVISIBLE BLUE™ A-594-5, combinations thereof, and the like. Other suitable fluorescent agents include, for example, 9,10-diphenyl anthracene and its derivatives, N-salicylidene-4-dimethylaminoaniline, 2-(2-hydroxyphenyl)benimidazole, 2-(2-hydroxyphenyl)benzoxazole, combinations thereof, and the like.

Other various exemplary fluorescent colorants include fluorescent pigments, including carboxylic-indenofluorenone, such as monocarboxylic-indenofluorenone and dicarboxylic-indenofluorenone, and 2-(5-hydroxylpentyl)-1H-thioxantheno[2,1,9-def]isoquinoline-1,3(2H)-dione.
Fluorescent pigments also include various derivatized analogs, such as rhodamines, perylenes including C.I. Pigment Orange 43 and C.I. Pigment Red 194, perinones, squaraines, and BONA pigments such as C.I. Pigment Red 57 and C.I. Pigment Red 48.

Ester Monomers

In embodiments, the reaction solution includes an ester monomer The ester monomer may be a cyclic ester monomer. Any appropriate cyclic ester monomer may be used in the enzymatic polymerization, such as a cyclic ester having from 5 to 16 carbon atoms, such as 6 to 15 carbon atoms, 7 to 12 carbon atoms, or 8 to 10 carbon atoms. The cyclic ester monomer may be a lactone, lactide and macrolide, cyclic carbonate, cyclic phosphate, cyclic depsipeptide or oxirane. Illustrative examples of appropriate cyclic ester monomers include lactones, such as oxacycloheptadec-10-en-2-one (available as AMBRETTOLIDE, from Penta Manufacturing Co.), omega-pentadecalactone (available as EXALTOLIDE, from Penta Manufacturing Co.), pentadecalactone, 11/12-pentadecen-15-olide (also known as pentadecenlactone), hexadecenlactone and caprolactone. Other suitable ester monomers include β-propiolactone, β-butyrolactone, propylmalolactonate, 2-methylene-4-oxa-12-dodecanolide, poly (butadiene-b-pentadecalactone), poly(butadiene-b-∈-CL), ∈-caprolactone, (R) and (S)-3-methyl-4-oxa-6-hexanolide, 1,3-dioxane-2-one, 1,4-dioxane-2-one, 3(S)-isopropylmorpholine-2,5-dione, Morpholine-2,5-dione derivatives, trimethylene carbonate, 1-methyl trimethylene carbonate, 8-octanolide, δ-Decalactone, 12-Dodecanolide, α-Methylene macrolides, and α-Methylene-δ-valerolactone.

In embodiments, the reaction solution may include a non-cyclic ester monomer. Exemplary non-cyclic ester monomers include diacids, hydroxyl acids, and diesters. For example, suitable non-cyclic ester monomers that may be used include 10-hydroxy decanoic acid, 6-hydroxyhexanoic acid, 10-hydroxyhexadecanoic acid, 12-hydroxydodecanoic acid, 16-hydroxyhexadecanoic acid, 3-hydroxy butyric acid, divinyl dicarboxylates, such as divinyl adipate and divinyl sebacate, 2,2,2-trichloroethyl ester, 2,2,2-trifluoroethyl ester, unactivated diacids, such as succinic, glutaric, adipic and sebacic acids, 6-6'-O-divinyl adipate, α-ω-dixacarboxylic methyl ester, bis(hydroxylmethyl)butyric acid, and ω-fluoro-(ω-1)hydroxyl alkanoic acid.

The ester monomer may be provided to the reaction solution independently, or in the form of an organic solution comprising an ester monomer, The molar ratio of colorant to ester monomer in the reaction solution may be any effective ratio, such as about 1:1 to about 1:50, about 1:5 to about 1:45, about 1:10 to about 1:40, or about 1:15 to about 1:35. Variation in concentration of colorant to ester monomer can be used to control the molecular weight of the polymeric product.

Enzymes

The reaction solution further includes one or more appropriate enzymes. The one or more enzymes catalyze the reaction of a colorant and an ester monomer, and allow the polymerization to occur at low temperatures. An illustrative example of enzymes that can be used is a lipase, such as lipase PA, lipase PC, lipase PF, lipase A, lipase CA, lipase B (such as candita antartica lipase B), lipase CC, lipase K, lipase MM, cutinase or porcine lipase.

The enzymes may be present in the reaction solution in immobilized or supported (non-covalently bound enzymes, such as adsorbed enzymes or enzymes that are cross-linked to other enzymes) or both immobilized and supported or free form.

The one or more enzymes may be present in the reaction solution in any effective concentration, such as from about 0.001 g/cm$^3$ to about 0.060 g/cm$^3$, from about 0.004 g/cm$^3$ to about 0.040 g/cm$^3$, from about 0.006 g/cm$^3$ to about 0.020 g/cm$^3$, or from about 0.01 g/cm$^3$ to about 0.050 g/cm$^3$. The concentration of the one or more enzymes in the reaction solution may be controlled by varying the ratio of the mass of enzyme to the mass of an immobilizing agent, such as one or more of a cross-linked polymeric network, cross-linked polymeric beads, polymeric packings, membranes, silica-gel, silica beads, sand and zeolites.

Optional Reaction Components

The monomer may be provided to the reaction solution independently, or in the form of a monomer solution comprising monomer and a solvent. Solvents may be added to the reaction in order to help reduce the viscosity of the reaction medium to enable more facile stirring or pumping of the reaction solution.

The reaction solution may thus also comprise one or more suitable solvents, such as toluene, benzene, hexane and its analogs (such as heptane), and tetrahydrofuran and its analogs (such as 2-methyltetrahydrofuran), and methyl ethyl ketone and its analogs.

The solvent may be mixed with the monomer prior to or after addition of the monomer to the reaction solution. When present, the solvent may be of any appropriate concentration range relative to the content of monomer. For example, the solvent may comprise from 1% to about 99% of the total weight of the solvent and the cyclic monomer, such as from about 10% to about 90%, such as from about 25% to about 75%, such as from about 40% to about 60%, or such as about 50% of the total weight of the solvent and the monomer.

Reaction Conditions

The enzymatic polymerization can be undertaken at temperatures from about 50° C. to about 90° C., such as from about 55° C. to about 85° C., from about 60° C. to about 80° C., or from about 65° C. to about 75° C.

The method may be achieved through any appropriate enzymatic polymerization technique. The method may include bulk polymerization or solution polymerization, in either batch or continuous reactor configuration. In the later cases, the catalyst is packed in a column reactor and ester monomer is pumped through the catalyst to form polymer continuously. In the former case, the catalyst is added to the kettle and stirred along with the added ester monomer(s). In both cases, the colorant is added as a hydroxyl initiating site for the enzymatic polymerization. The ratio of colorant to ester monomer can be used to control the polymer molecular weight to some degree.

Bulk polymerization of polyesters in a continuous packed-bed reactor using immobilized enzyme catalysts is further disclosed in U.S. application Ser. No. 12/240,421, which is hereby incorporated herein in its entirety by reference.

Reaction Products: Colorant-Polyesters and Polyesters

In embodiments, the enzymatic polymerization reaction produces a reaction product comprising polymeric mixture (polymeric product). The reaction product may include both colorant-polyester polymers and polyester polymers formed without covalently linked colorant (hereinafter "non-colorant polyester"). The colorant-polyester polymer comprises at least one colorant and at least one polyester resin, where the colorant is covalently linked to the polyester resin. The colorant may be covalently linked to the polyester resin at an α-position.

The polyester resin (as a part of colorant-polyester or polyester formed without linked colorant) is formed by polymerization of ester monomers. The structure of the formed polyester is dependent on the monomer(s) used in the reaction. An exemplary structure of a polyester resin is expressed by the following reaction-structure model:

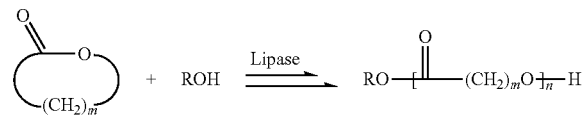

where R may be a colorant and m may be from 4 to 15. Other various structures are possible by using any of the ester monomers described above.

A non-colorant polyester polymer may also be used for its physical, mechanical, rheological, and/or thermal properties. A non-colorant polyester polymer may, for example, have the desired physical properties for a particular application and, at the same time, serve as a diluent (matrix) for the colorant-polyester polymer. A non-colorant polyester polymer therefore may help, for example, reduce the concentration of the colorant-polyester polymer in the final product to a concentration desired for a particular application without affecting the other desired properties of the material.

In embodiments, the reaction product may include different colorant-polyester polymers, with different colorants linked to different polyester molecules.

The colorant-polyester polymers may be of any appropriate weight average molecular weight ($M_w$), such as from about 1,000 g/mol to about 50,000 g/mol, from about 2,000 g/mol to about 25,000 g/mol, from about 5,000 g/mol to about 20,000 g/mol, or from about 5,000 g/mol to about 10,000 g/mol, as measured by differential scanning-calorimetry (DSC).

The colorant-polyester polymers may be of any appropriate number average molecular weight ($M_n$), such as about 1,000 g/mol to about 50,000 g/mol, from about 2,000 g/mol to about 25,000 g/mol, from 5,000 g/mol to about 20,000 g/mol, or from about 5,000 g/mol to about 10,000 g/mol, as measured by Gel Permeation Chromatography (GPC).

The colorant-polyester polymers may be of any appropriate polydispersity index ($M_w/M_n$) (PDT), such as from about 1.00 to about 2.50, from about 1.25 to about 2.00, from about 1.50 to about 1.75, or from about 1.40 to about 1.60.

The colorant-polyester polymers may be in any structural form, such as amorphous or crystalline, depending on the types of monomers used to produce the polyester.

The colorant-polyester polymer synthesized using a fluorescent colorant via the enzymatic polymerization retains its fluorescent behavior as observed visually and can be used as a colorant for various applications.

In embodiments, a latex emulsion of the colorant-polyester polymer and non-colorant polyester polymer mixture may be formed by phase inversion emulsification methods. Utilizing such methods, the colorant-polyester polymer may be present in a colorant-polyester polymer emulsion, which may then be combined with other components and additives to form a toner of the present disclosure.

Toner

The colorant-polyester polymers described herein may be utilized in toners. In embodiments, the toner includes a colorant-polyester polymer in a toner vehicle, optionally with one or more other colorants, optionally with one or more toner additives. The colorant-polyester polymers described herein may be utilized with toners produced by chemical synthesis methods, including emulsion aggregation toners and toners produced in suspensions, by chemical milling, combinations thereof, and the like. The toner may be obtained, for example, by conventional processes wherein a resin is melt kneaded or extruded with a pigment, micronized, and pulverized to provide toner particles. Such processes are illustrated in U.S. Pat. Nos. 5,364,729 and 5,403,693, the disclosures of each of which are hereby incorporated by reference in their entirety.

In embodiments, the colorant-polyester is included in the toner in an amount of from, for example, about 0.01 to about 15% by weight of the toner, such as about 0.1 to about 6%, or about 0.1 to about 3%.

The emulsions as described above may be utilized to form toner compositions by any method within the purview of those skilled in the art. The latex emulsion may be contacted with a colorant, optionally in a dispersion, a defoamer, and other additives to form a toner by a suitable process, in embodiments, an emulsion aggregation and coalescence process.

In embodiments, the optional additional ingredients of a toner composition including colorant, wax, and other additives may be added before, during or after the melt mixing the resin to form the latex. The additional ingredients may be added before, during or after the formation of the latex emulsion, wherein the neutralized resin is contacted with water. In further embodiments, the colorant may be added before the addition of a surfactant.

Surfactants

In embodiments, the colorant-polyester polymer, additional colorants, waxes, and other additives utilized to form toner compositions may be in dispersions including surfactants. Moreover, toner particles may be formed by emulsion aggregation methods where the resin and other components of the toner are placed in one or more surfactants, an emulsion is formed, toner particles are aggregated, coalesced, optionally washed and dried, and recovered.

One, two, or more surfactants may be utilized. The surfactants may be selected from ionic surfactants and nonionic surfactants. Anionic surfactants and cationic surfactants are encompassed by the term "ionic surfactants." In embodiments, the surfactant may be added as a solid or as a highly concentrated solution with a concentration of from about 10% to about 100% (pure surfactant) by weight, in embodiments, from about 15% to about 75% by weight.

In embodiments, the surfactant may be utilized so that it is present in an amount of from about 0.01% to about 5% by weight of the toner composition, for example from about 0.75% to about 4% by weight of the toner composition, in embodiments from about 1% to about 3% by weight of the toner composition.

Examples of nonionic surfactants that can be utilized include, for example, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy)ethanol, available from Rhone-Poulenc as IGEPAL CA-210™, IGEPAL CA-520™, IGEPAL CA-720™, IGEPAL CO-890™, IGEPAL CO-720™, IGEPAL CO-290™, IGEPAL CA-210™, ANTAROX 890™ and ANTAROX 897™, Other examples of suitable nonionic surfactants include a block copolymer of polyethylene oxide and polypropylene oxide, including those commercially available as SYNPERONIC PE/F, in embodiments SYNPERONIC PE/F 108. Combinations of these surfactants and any of the foregoing nonionic surfactants may be utilized in embodiments.

Anionic surfactants which may be utilized include sulfates and sulfonates, sodium dodecylsulfate (SDS), sodium dodecylbenzene sulfonate, sodium dodecylnaphthalene sulfate, dialkyl benzenealkyl sulfates and sulfonates, acids such as abitic acid available from Aldrich, NEOGEN R™, NEOGEN SC™ obtained from Daiichi Kogyo Seiyaku, combinations thereof, and the like. Other suitable anionic surfactants include, in embodiments, DOWFAX™ 2A1, an alkyldiphenyloxide disulfonate from The Dow Chemical Company, and/or TAYCA POWER BN2060 from Tayca Corporation (Japan), which are branched sodium dodecyl benzene sulfonates. Combinations of these surfactants and any of the foregoing anionic surfactants may be utilized in embodiments.

Examples of the cationic surfactants, which are usually positively charged, include, for example, alkylbenzyl dimethyl ammonium chloride, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, $C_{12}$, $C_{15}$, $C_{17}$ trimethyl ammonium bromides, halide salts of quaternized polyoxyethylalkylamines, dodecylbenzyl triethyl ammonium chloride, MIRAPOL™ and ALKAQUAT™, available from Alkaril Chemical Company, SANIZOL™ (benzalkonium chloride), available from Kao Chemicals, and the like, and mixtures thereof.

Colorants

In addition to the colorant present in the colorant-polyester polymer, the toner composition may optionally comprise additional colorants, such as dyes, pigments, mixtures of dyes, mixtures of pigments, mixtures of dyes and pigments, and the like. In embodiments, the additional colorant may be included in the toner in an amount of, for example, about 0.1 to about 35% by weight of the toner, or from about 1 to about 15% by weight of the toner, or from about 1 to about 10% by weight of the toner.

As examples of suitable colorants, mention may be made of carbon black like REGAL 330® (Cabot), Carbon Black 5250 and 5750 (Columbian Chemicals), Sunsperse Carbon Black LHD 9303 (Sun Chemicals); magnetites, such as Mobay magnetites MO8029™, MO8060™; Columbian magnetites; MAPICO BLACKS™ and surface treated magnetites; Pfizer magnetites CB4799™, CB5300™, CB5600™, MCX6369™; Bayer magnetites, BAYFERROX 8600™, 8610™; Northern Pigments magnetites, NP-604™, NP608™; Magnox magnetites TMB-100™, or TMB-104™; and the like. As colored pigments, there can be selected cyan, magenta, yellow, red, green, brown, blue or mixtures thereof. Generally, cyan, magenta, or yellow pigments or dyes, or mixtures thereof, are used. The pigment or pigments are generally used as water based pigment dispersions.

In general, suitable colorants may include Paliogen Violet 5100 and 5890 (BASF), Normandy Magenta RD-2400 (Paul Uhlrich), Permanent Violet VT2645 (Paul Uhlrich), Heliogen Green L8730 (BASF), Argyle Green XP-111-S (Paul Uhlrich), Brilliant Green Toner GR 0991 (Paul Uhlrich), Lithol Scarlet D3700 (BASF), Toluidine Red (Aldrich), Scarlet for Thermoplast NSD PS PA (Ugine Kuhlmann of Canada), Lithol Rubine Toner (Paul Uhlrich), Lithol Scarlet 4440 (BASF), NBD 3700 (BASF), Bon Red C (Dominion Color), Royal Brilliant Red RD-8192 (Paul Uhlrich), Oracet Pink RF (Ciba Geigy), Paliogen Red 3340 and 3871K (BASF), Lithol Fast Scarlet L4300 (BASF), Heliogen Blue D6840, D7080, K7090, K6910 and L7020 (BASF), Sudan Blue OS (BASF), Neopen Blue FF4012 (BASF), PV Fast Blue B2G01 (American Hoechst), Irgalite Blue BCA (Ciba Geigy), Paliogen Blue 6470 (BASF), Sudan II, III and IV (Matheson, Coleman, Bell), Sudan Orange (Aldrich), Sudan Orange 220 (BASF), Paliogen Orange 3040 (BASF), Ortho Orange OR 2673 (Paul Uhlrich), Paliogen Yellow 152 and 1560 (BASF), Lithol Fast Yellow 0991K (BASF), Paliotol Yellow 1840 (BASF), Novaperm Yellow FGL (Hoechst), Permanerit Yellow YE 0305 (Paul Uhlrich), Lumogen Yellow D0790 (BASF), Sunsperse Yellow YHD 6001 (Sun Chemicals), Suco-Gelb 1250 (BASF), Suco-Yellow D1355 (BASF), Suco Fast Yellow D1165, D1355 and D1351 (BASF), Hostaperm Pink E™ (Hoechst), Fanal Pink D4830 (BASF), Cinquasia Magenta™ (DuPont), Paliogen Black L9984 (BASF), Pigment Black K801 (BASF), Levanyl Black A-SF (Miles, Bayer), combinations of the foregoing, and the like.

Other suitable water based colorant dispersions include those commercially available from Clariant, for example, Hostafine Yellow GR, Hostafine Black T and Black TS, Hostafine Blue B2G, Hostafine Rubine F6B and magenta dry pigment such as Toner Magenta 6BVP2213 and Toner Magenta EO2 which may be dispersed in water and/or surfactant prior to use.

Specific examples of pigments include Sunsperse BHD 6011X (Blue 15 Type), Sunsperse BHD 9312X (Pigment Blue 15 74160), Sunsperse BHD 6000X (Pigment Blue 15:3 74160), Sunsperse GHD 9600X and GHD 6004X (Pigment Green 7 74260), Sunsperse QHD 6040X (Pigment Red 122 73915), Sunsperse RHD 9668X (Pigment Red 185 12516), Sunsperse RHD 9365X and 9504X (Pigment Red 57 15850: 1, Sunsperse YHD 6005X (Pigment Yellow 83 21108), Flexiverse YFD 4249 (Pigment Yellow 17 21105), Sunsperse YHD 6020X and 6045X (Pigment Yellow 74 11741), Sunsperse YHD 600X and 9604X (Pigment Yellow 14 21095), Flexiverse LFD 4343 and LFD 9736 (Pigment Black 7 77226), Aquatone, combinations thereof, and the like, as water based pigment dispersions from Sun Chemicals, Heliogen Blue L6900™, D6840™, D7080™, D7020™, Pylam Oil Blue™, Pylam Oil Yellow™, Pigment Blue 1™ available from Paul Uhlich & Company, Inc., Pigment Violet 1™, Pigment Red 48™, Lemon Chrome Yellow DCC 1026™, E.D. Toluidine Red™ and Bon Red C™ available from Dominion Color Corporation, Ltd., Toronto, Ontario, Novaperm Yellow FGL™, and the like. Generally, colorants that can be selected are black, cyan, magenta, or yellow, and mixtures thereof. Examples of magentas are 2,9-dimethyl-substituted quinacridone and anthraquinone dye identified in the Color Index as CI-60710, CI Dispersed Red 15, diazo dye identified in the Color Index as CI-26050, CI Solvent Red 19, and the like. Illustrative examples of cyans include copper tetra(octadecyl sulfonamido) phthalocyanine, x-copper phthalocyanine pigment listed in the Color Index as CI-74160, CI Pigment Blue, Pigment Blue 15:3, and Anthrathrene Blue, identified in the Color Index as CI-69810, Special Blue X-2137, and the like. Illustrative examples of yellows are diarylide yellow 3,3-dichlorobenzidene acetoacetanilides, a monoazo pigment identified in the Color Index as CI 12700, CI Solvent Yellow 16, a nitrophenyl amine sulfonamide identified in the Color Index as Foron Yellow SE/GLN, CI Dispersed Yellow 33 2,5-dimethoxy-4-sulfonanilide phenylazo-4'-chloro-2,5-dimethoxy acetoacetanilide, and Permanent Yellow FGL.

In embodiments, the colorant may include a pigment, a dye, combinations thereof, carbon black, magnetite, black, cyan, magenta, yellow, red, green, blue, brown, combinations thereof, in an amount sufficient to impart the desired color to the toner. It is to be understood that other useful colorants will become readily apparent based on the present disclosures.

Wax

Optionally, a wax may also be combined with the colorant-polyester polymer in forming toner particles. The wax may be provided in a wax dispersion, which may include a single type of wax or a mixture of two or more different waxes. A single wax may be added to toner formulations, for example, to improve particular toner properties, such as toner particle shape, presence and amount of wax on the toner particle surface, charging and/or fusing characteristics, gloss, stripping, offset properties, and the like. Alternatively, a combination of waxes can be added to provide multiple properties to the toner composition.

When included, the wax may be present in an amount of, for example, from about 1 weight percent to about 25 weight percent of the toner particles, in embodiments from about 5 weight percent to about 20 weight percent of the toner particles.

When a wax dispersion is used, the wax dispersion may include any of the various waxes conventionally used in emulsion aggregation toner compositions. Waxes that may be selected include waxes having, for example, $M_w$ of from about 500 g/mol to about 20,000 g/mol, such as from about 1,000 g/mol to about 10,000 g/mol, or from about 1,500 g/mol to about 5,000 g/mol, as measured by GPC. Waxes that may be used include, for example, polyolefins such as polyethylene, polypropylene, and polybutene waxes such as commercially available from Allied Chemical and Petrolite Corporation, for example POLYWAX™ polyethylene waxes from Baker Petrolite, wax emulsions available from Michaelman, Inc. and the Daniels Products Company, EPOLENE N-15™ commercially available from Eastman Chemical Products, Inc., and VISCOL 550-P™, a low weight average molecular weight polypropylene available from Sanyo Kasei K. K.; plant-based waxes, such as carnauba wax, rice wax, candelilla wax, sumacs wax, and jojoba oil; animal-based waxes, such as beeswax; mineral-based waxes and petroleum-based waxes, such as montan wax, ozokerite, ceresin, paraffin wax, microcrystalline wax, and Fischer-Tropsch wax; ester waxes obtained from higher fatty acid and higher alcohol, such as stearyl stearate and behenyl behenate; ester waxes obtained from higher fatty acid and monovalent or multivalent lower alcohol, such as butyl stearate, propyl oleate, glyceride monostearate, glyceride distearate, and pentaerythritol tetra behenate; ester waxes obtained from higher fatty acid and multivalent alcohol multimers, such as diethyleneglycol monostearate, dipropyleneglycol distearate, diglyceryl distearate, and triglyceryl tetrastearate; sorbitan higher fatty acid ester waxes, such as sorbitan monostearate, and cholesterol higher fatty acid ester waxes, such as cholesteryl stearate. Examples of functionalized waxes that may be used include, for example, amines, amides, for example AQUA SUPER-SLIP 6550™, SUPERSLIP 6530™ available from Micro Powder Inc., fluorinated waxes, for example POLYFLUO 190™, POLYFLUO 200™, POLYSILK 19™, POLYSILK 14™ available from Micro Powder Inc., mixed fluorinated, amide waxes, for example MICROSPERSION 19™ also available from Micro Powder Inc., imides, esters, quaternary amines, carboxylic acids or acrylic polymer emulsion, for example JONCRYL 74™, 89™, 130™, 537™, and 538™, all available from SC Johnson Wax, and chlorinated polypropylenes and polyethylenes available from Allied Chemical and Petrolite Corporation and SC Johnson wax. Mixtures and combinations of the foregoing waxes may also be used in embodiments. Waxes may be included as, for example, fuser roll release agents. In embodiments, the waxes may be crystalline or non-crystalline.

In embodiments, the wax may be incorporated into the toner in the form of one or more aqueous emulsions or dispersions of solid wax in water, where the solid wax particle size may be in the range of from about 100 to about 300 nm.

Core Resin

The toner particles may be prepared by any method within the purview of one skilled in the art. Although embodiments relating to toner particle production are described below with respect to emulsion aggregation processes, any suitable method of preparing toner particles may be used, including chemical processes, such as suspension and encapsulation processes disclosed in U.S. Pat. Nos. 5,290,654 and 5,302,486, the disclosures of each of which are hereby incorporated by reference in their entirety. In embodiments, toner compositions and toner particles may be prepared by aggregation and coalescence processes in which small-size resin particles are aggregated to the appropriate toner particle size and then coalesced to achieve the final toner-particle shape and morphology.

In embodiments, toner compositions may be prepared by emulsion aggregation processes, such as a process that includes aggregating a mixture of an optional colorant, an optional wax and any other desired or required additives, and emulsions including the colorant-polyester polymer described above, optionally in surfactants as described above, and then coalescing the aggregate mixture. A mixture may be prepared by adding an optional colorant and optional wax or other materials, which may also be optionally in a dispersion(s) including a surfactant, to the colorant-polyester emulsion, which may be a mixture of two or more emulsions containing resin. The pH of the resulting mixture may be adjusted by an acid such as, for example, acetic acid, nitric acid or the like. In embodiments, the pH of the mixture may be adjusted to from about 2 to about 5. Additionally, in embodiments, the mixture may be homogenized. If the mixture is homogenized, homogenization may be accomplished by mixing at about 600 to about 6,000 revolutions per minute. Homogenization may be accomplished by any suitable means, including, for example, an IKA ULTRA TURRAX T50 probe homogenizer.

Following the preparation of the above mixture, an aggregating agent may be added to the mixture. Any suitable aggregating agent may be utilized to form a toner. Suitable aggregating agents include, for example, aqueous solutions of a divalent cation or a multivalent cation material. The aggregating agent may be, for example, an inorganic cationic aggregating agent such as polyaluminum halides such as polyaluminum chloride (PAC), or the corresponding bromide, fluoride, or iodide, polyaluminum silicates such as polyaluminum sulfosilicate (PASS), and water soluble metal salts including aluminum chloride, aluminum nitrite, aluminum sulfate, potassium aluminum sulfate, calcium acetate, calcium chloride, calcium nitrite, calcium oxylate, calcium sulfate, magnesium acetate, magnesium nitrate, magnesium sulfate, zinc acetate, zinc nitrate, zinc sulfate, zinc chloride, zinc bromide, magnesium bromide, copper chloride, copper sulfate, and combinations thereof. In embodiments, the aggregating agent may be added to the mixture at a temperature that is below the glass transition temperature (Tg) of the colorant-polyester.

Suitable examples of organic cationic aggregating agents include, for example, dialkyl benzenealkyl ammonium chloride, lauryl trimethyl ammonium chloride, alkylbenzyl methyl ammonium chloride, alkyl benzyl dimethyl ammonium bromide, benzalkonium chloride, cetyl pyridinium bromide, $C_{12}$, $C_{15}$, $C_{17}$ trimethyl ammonium bromides, halide salts of quaternized polyoxyethylalkylamines, dodecylbenzyl triethyl ammonium chloride, and the like, and mixtures thereof.

Other suitable aggregating agents also include, but are not limited to, tetraalkyl titinates, dialkyltin oxide, tetraalkyltin oxide hydroxide, dialkyltin oxide hydroxide, aluminum alkoxides, alkylzinc, dialkyl zinc, zinc oxides, stannous oxide, dibutyltin oxide, dibutyltin oxide hydroxide, tetraalkyl tin, and the like. Where the aggregating agent is a polyion aggregating agent, the agent may have any desired number of polyion atoms present. For example, in embodiments, suitable polyaluminum compounds have from about 2 to about 13, in other embodiments, from about 3 to about 8, aluminum ions present in the compound.

The aggregating agent may be added to the mixture utilized to form a toner in an amount of, for example, from about 0% to about 10% by weight, in embodiments from about 0.2% to about 8% by weight, in other embodiments from about 0.5% to about 5% by weight, of the resin in the mixture, although the amount of aggregating agent can be outside of these ranges. This should provide a sufficient amount of agent for aggregation.

The particles may be permitted to aggregate until a predetermined desired particle size is obtained. A predetermined desired size refers to the desired particle size to be obtained as determined prior to formation, and the particle size being monitored during the growth process until such particle size is reached. Samples may be taken during the growth process and analyzed, for example with a Coulter Counter, for average particle size. The aggregation thus may proceed by maintaining the elevated temperature, or slowly raising the temperature to, for example, from about 40° C. to about 100° C., and holding the mixture at this temperature for a time of from about 0.5 hours to about 6 hours, in embodiments from about hour 1 to about 5 hours, while maintaining stirring, to provide the aggregated particles. Once the predetermined desired particle size is reached, then the growth process is halted.

The growth and shaping of the particles following addition of the aggregation agent may be accomplished under any suitable conditions. For example, the growth and shaping may be conducted under conditions in which aggregation occurs separate from coalescence. For separate aggregation and coalescence stages, the aggregation process may be conducted under shearing conditions at an elevated temperature, for example of from about 40° C. to about 90° C., in embodiments from about 45° C. to about 80° C., which may be below the glass transition temperature of the colorant-polyester as discussed above.

Once the desired final size of the toner particles is achieved, the pH of the mixture may be adjusted with a base to a value of from about 3 to about 10, and in embodiments from about 5 to about 9. The adjustment of the pH may be utilized to freeze, that is to stop, toner growth. The base utilized to stop toner growth may include any suitable base such as, for example, alkali metal hydroxides such as, for example, sodium hydroxide, potassium hydroxide, ammonium hydroxide, combinations thereof, and the like. In embodiments, ethylene diamine tetraacetic acid (EDTA) may be added to help adjust the pH to the desired values noted above.

Shell Resin

In embodiments, after aggregation, but prior to coalescence, a resin coating may be applied to the aggregated particles to form a shell thereover. Any resin, including the colorant-polyester polymer described above, as suitable for forming the core resin may be utilized as the shell.

In embodiments, resins which may be utilized to form a shell include, but are not limited to, a crystalline resin latex, and/or amorphous resins that may be formed by, for example, a phase inversion emulsification process. In embodiments, an amorphous resin that may be utilized to form a shell in accordance with the present disclosure includes an amorphous polyester, optionally in combination with a crystalline polyester resin latex. Multiple resins may be utilized in any suitable amounts. A first resin may be present in an amount of from about 20 percent by weight to about 100 percent by weight of the total shell resin, in embodiments from about 30 percent by weight to about 90 percent by weight of the total shell resin. Thus, a second resin may be present in the shell resin in an amount of from about 0 percent by weight to about 80 percent by weight of the total shell resin, such as from about 10 percent by weight to about 70 percent by weight of the shell resin.

The shell resin may be applied to the aggregated particles by any method within the purview of those skilled in the art. In embodiments, the resins utilized to form the shell may be in an emulsion including any surfactant described above. The emulsion possessing the resins may be combined with the aggregated particles described above so that the shell forms over the aggregated particles.

The formation of the shell over the aggregated particles may occur while heating to a temperature of from about 30° C. to about 80° C., in embodiments from about 35° C. to about 70° C. The formation of the shell may take place for a period of time of from about 5 minutes to about 10 hours, such as from about 10 minutes to about 5 hours.

Coalescence

Following aggregation to the desired particle size and application of any optional shell, the particles may then be coalesced to the desired final shape, the coalescence being achieved by, for example, heating the mixture to a temperature of from about 45° C. to about 100° C., such as from about 55° C. to about 99° C., which may be at or above the glass transition temperature of the resins utilized to form the toner particles, and/or reducing the stirring, for example to from about 100 rpm to about 1,000 rpm, such as from about 200 rpm to about 800 rpm. Coalescence may be accomplished over a period of from about 0.01 to about 9 hours, in embodiments from about 0.1 to about 4 hours.

After aggregation and/or coalescence, the mixture may be cooled to room temperature, such as from about 20° C. to about 25° C. The cooling may be rapid or slow, as desired. A suitable cooling method may include introducing cold water to a jacket around the reactor. After cooling, the toner particles may be optionally washed with water, and then dried. Drying may be accomplished by any suitable method for drying including, for example, freeze-drying.

Additives

In embodiments, the toner particles may also contain other optional additives, as desired or required. For example, the toner may include positive or negative charge control agents, for example in an amount of from about 0.1 to about 10% by weight of the toner, in embodiments from about 1 to about 3% by weight of the toner. Examples of suitable charge control agents include quaternary ammonium compounds inclusive of alkyl pyridinium halides; bisulfates; alkyl pyridinium compounds, including those disclosed in U.S. Pat. No. 4,298,672, the disclosure of which is hereby incorporated by reference in its entirety; organic sulfate and sulfonate compositions, including those disclosed in U.S. Pat. No. 4,338,390, the disclosure of which is hereby incorporated by reference in its entirety; cetyl pyridinium tetrafluoroborates; distearyl dimethyl ammonium methyl sulfate; aluminum salts such as BONTRON E84™ or E88™ (Orient Chemical Industries, Ltd.); combinations thereof, and the like.

There can also be blended with the toner particles external additive particles after formation including flow aid additives, which additives may be present on the surface of the toner particles. Examples of these additives include metal oxides such as titanium oxide, silicon oxide, aluminum oxides, cerium oxides, tin oxide, mixtures thereof, and the like; colloidal and amorphous silicas, such as AEROSIL®, metal salts and metal salts of fatty acids inclusive of zinc stearate, calcium stearate, or long chain alcohols such as UNILIN 700, and mixtures thereof.

In general, silica may be applied to the toner surface for toner flow, tribo enhancement, admix control, improved development and transfer stability, and higher toner blocking temperature. $TiO_2$ may be applied for improved relative humidity (RH) stability, tribo control and improved development and transfer stability. Zinc stearate, calcium stearate and/or magnesium stearate may optionally also be used as an external additive for providing lubricating properties, developer conductivity, tribo enhancement, enabling higher toner charge and charge stability by increasing the number of contacts between toner and carrier particles. In embodiments, a commercially available zinc stearate known as Zinc Stearate L (obtained from Ferro Corporation) may be used. The external surface additives may be used with or without a coating.

Each of these external additives may be present in an amount of from about 0.1% by weight to about 5% by weight of the toner, in embodiments of from about 0.25% by weight to about 3% by weight of the toner, although the amount of additives can be outside of these ranges. In embodiments, the toners may include, for example, from about 0.1% by weight to about 5% by weight titania, from about 0.1% by weight to about 8% by weight silica, and from about 0.1% by weight to about 4% by weight zinc stearate.

Suitable additives include those disclosed in U.S. Pat. Nos. 3,590,000, 3,800,588, and 6,214,507, the disclosures of each of which are hereby incorporated by reference in their entirety.

In embodiments, the toner of the present disclosure may have the following properties:

(1) Volume average diameter (also referred to as "volume average particle diameter") of from about 3 to about 25 µm, or from about 4 to about 15 µm, or from about 4.5 to about 10 µm.

(2) Number Average Geometric Size Distribution (GSDn) and/or Volume Average Geometric Size Distribution (GSDv) of from about 1.05 to about 1.55, such as from about 1.1 to about 1.4, from about 1.15 to about 1.35, or from about 1.20 to about 1.30.

(3) Circularity of from about 0.93 to about 1, such as from about 0.94 to about 0.99, from about 0.95 to about 0.98, or from about 0.96 to about 0.97.

(4) Coarse content of from about 0.01% to about 10%, such as of from about 0.1% to about 5%, from about 0.3% to about 3%, or from about 0.5% to about 2%.

The characteristics of the toner particles may be determined by any suitable technique and apparatus. Volume average particle diameter $D_{50}v$, GSDv, and GSDn may be measured by means of a measuring instrument such as a Beckman Coulter Multisizer 3, operated in accordance with the manufacturer's instructions. The GSDv refers to the upper geometric standard deviation (GSDv) by volume (coarse level) for (D84/D50). The GSDn refers to the geometric standard deviation (GSDn) by number (fines level) for (D50/D16). The particle diameters at which a cumulative percentage of 50% of the total toner particles are attained are defined as volume D50, and the particle diameters at which a cumulative percentage of 84% are attained are defined as volume D84. These aforementioned volume average particle size distribution indexes GSDv can be expressed by using D50 and D84 in cumulative distribution, wherein the volume average particle size distribution index GSDv is expressed as (volume D84/volume D50). These aforementioned number average particle size distribution indexes GSDn can be expressed by using D50 and D16 in cumulative distribution, wherein the number average particle size distribution index GSDn is expressed as (number D50/number D16). The closer to 1.0 that the GSD value is, the less size dispersion there is among the particles. The aforementioned GSD value for the toner particles indicates that the toner particles are made to have a narrow particle size distribution.

Representative sampling may occur as follows: a small amount of toner sample, about 1 g, may be obtained and filtered through a 25 µm screen, then put in isotonic solution to obtain a concentration of about 10%, with the sample then run in a Beckman Coulter Multisizer 3.

The circularity of the toner particles may be determined by any suitable technique and apparatus. The circularity is a measure of the particles closeness to perfectly spherical. A circularity of 1.0 identifies a particle having the shape of a perfect circular sphere. Volume average circularity may be measured by means of a measuring instrument such as a Flow Particle Image Analysis (FPIA) such as for example the Sysmex® Flow Particle Image Analyzer, commercially available from Sysmex Corporation, operated in accordance with the manufacturer's instructions. Representative sampling may occur as follows: about 0.5 g of toner sample may be obtained and filtered through a 25 μm screen, then put in deionized water to obtain a concentration of about 5%, with the sample then run in a Flow Particle Image Analyzer.

The coarse content of the toner particles may be determined by any suitable technique and apparatus. Coarse content may be measured by means of wet sieving using a sieve and collecting the coarse or a measuring instrument such as a coulter counter, such as the Beckman Coulter Counter Multisizer 3, commercially available from Beckman Coulter, operated in accordance with the manufacturer's instructions. Representative sampling may occur as follows: a small amount of toner sample, about 1 g, may be obtained and filtered through a 25 μm screen, then put in isotonic solution to obtain a concentration of about 10%, with the sample then run in a Beckman Coulter Multisizer 3.

Powder Coating

The above-discussed latex emulsion of the colorant polyester polymer and/or non-colorant polyester polymer mixture may be used to form a powder coating composition. Powder coating materials are solid compositions that are generally applied by an electrostatic spray process in which the powder coating particles are electrostatically charged by the spray gun and the substrate (normally metallic) is earthed. The charge on the powder coating particles is normally applied by interaction of the particles with ionized air (corona charging) or by friction (tribostatic or "tribo" charging). The charged particles are transported in air towards the substrate and their final deposition is influenced inter alia by the electric field lines that are generated between the spray gun and the work piece, as well as the space charge electric field from the charged powder cloud.

Powder coating compositions may comprise the colorant-polyester polymer described above, one or more colorants such as pigments, and one or more additives, such as magnetites, fillers, flocculants, curing agents, leveling agents, charge additives, flow-promoting agents, flow-control agents, plasticizers, stabilizers, anti-gassing agents, antioxidants, UV absorbing agents, light stabilizers and waxes.

In addition to the colorant-polyester polymer described above, the powder coating composition may optionally comprise additional resins, such as thermoset resins. These resins typically chemically react during baking to form a polymer network that will generally not re-melt. Thermoset powder coatings for materials or objects of metal are known. Materials utilized in thermoset powder coatings include epoxy resins, polyester resins and acrylic resins.

Thermoplastic resins are also appropriate for some powder coating applications and are generally of high molecular weight and require relatively high temperatures to achieve melt and flow during coating. However, the molecular weight and melt viscosity remain constant during the coating procedure so that the polymer can be easily re-melted for easy repair or touch-up. Thermoplastic coating polymers include, but are not limited to, polyamides, polyolefins, plasticized PVC, polyester and poly(vinylidene fluoride), ionomers, styrenes, copolymers comprising styrene and an acrylic ester, and the like.

Curable resins may be used in embodiments. Exemplary suitable curable resins include epoxy resins, poly-functional epoxy resins, polyester resins, carboxy-functional polyester resins, hydroxy-functional polyester resins, polyol resins, polycarboxylic acid resins and poly(vinylidene fluoride) resins.

In embodiments, powder coating compositions are prepared using suitable thermoset polymer resins. In embodiments, suitable thermoset powder compositions are adapted from systems such as, for example, carboxyl-terminated branched polyesters in combination with multifunctional epoxy resins, such as those described in U.S. Pat. No. 6,228,941; carboxyl-functionalized acrylic resins compounded with multifunctional epoxy resins, such as those described in Japanese patent application publication JP 2001-123110; epoxy resins or epoxy-functionalized acrylic resins in combination with latent polyfunctional amine catalysts, such as those described in U.S. Pat. No. 6,197,883 and European Patent EP 1 055 694 A2; blocked isocyanates in combination with hydroxyl-functionalized polyesters or acrylics, such as those described in WO 94/10221, Japanese patent application publication JP 2000-160061 and German Patent DE 198 04 281 A1; epoxy functionalized resins in combination with polycarboxylic acid cross-linking agents, such as those described in U.S. Pat. No. 6,218,483; macrocyclic esters, carbonates, amides or imides, ring-opened and polymerized in the present of polyfunctional epoxy resins, such as those described in European Patent EP 1 111 012 A1; mixtures thereof, and the like. The entire disclosures of the above-cited references are incorporated herein by reference.

In embodiments, thermally cross-linkable resins such as carboxyl- and hydroxyl-functionalized polyester and acrylic resins, epoxy resins and epoxy-functionalized acrylic resins, blocked isocyanates, hydroxyl-functionalized polyesters or acrylics, polycarboxylic acid cross-linking agents, macrocyclic esters, carbonates, amides or imides and polyfunctional epoxy resins, which can be obtained commercially, are used. In embodiments of the invention, commercially available polyfunctional amine catalysts are used.

The powder coating composition may, for example, be based on a solid polymeric binder system comprising a carboxy-functional polyester film-forming resin used with a polyepoxide curing agent. Such carboxy-functional polyester systems are currently the most widely used powder coatings materials. The polyester generally has an acid value in the range 10-100, a number average molecular weight Mn of 1,500 to 10,000 and a glass transition temperature Tg of from 30° C. to 85° C., preferably at least 40° C. The polyepoxide can, for example, be a low molecular weight epoxy compound such as triglycidyl isocyanurate (TGIC), a compound such as diglycidyl terephthalate or diglycidyl isophthalate, an epoxy resin such as a condensed glycidyl ether of bisphenol A or a light-stable epoxy resin. Such a carboxy-functional polyester film-forming resin can alternatively be used with a bis-(beta-hydroxyalkylamide) curing agent such as tetrakis(2-hydroxyethyl)adipamide.

An epoxy resin can also be used with an amine-functional curing agent such as, for example, dicyandiamide. Instead of an amine-functional curing agent for an epoxy resin, a phenolic material may be used, such as a material formed by reaction of epichlorohydrin with an excess of bisphenol A (that is to say, a polyphenol made by adducting bisphenol A and an epoxy resin). A functional acrylic resin, for example a carboxy-, hydroxy- or epoxy-functional resin can be used with an appropriate curing agent. Mixtures of binders can be used, for example a carboxy-functional polyester can be used with a carboxy-functional acrylic resin and a curing agent such as a bis-(beta-hydroxyalkylamide) which serves to cure both polymers. As further possibilities, for mixed binder systems, a carboxy-, hydroxy- or epoxy-functional acrylic resin may be used with an epoxy resin or a polyester resin (carboxy- or hydroxy-functional). Such resin combinations may be selected so as to be co-curing, for example, a carboxy-functional acrylic resin co-cured with an epoxy resin, or a carboxy-functional polyester co-cured with a glycidyl-functional acrylic resin. For example, such mixed binder systems are formulated so as to be cured with a single curing agent (for example, use of a blocked isocyanate to cure a hydroxy-functional acrylic resin and a hydroxy-functional polyester). Another formulation involves the use of a different curing agent for each binder of a mixture of two polymeric binders (for example, an amine-cured epoxy resin used in conjunction with a blocked isocyanate-cured hydroxy-functional acrylic resin).

The latex emulsion of resin may be formed by forming a latex of at least one resin, selected from those described above, in water. The resin may be prepared in bulk polymerization or by polycondensation process, and wherein the said resin is rendered hydrophilic by incorporation of alkali sulfonated monomers, for instance, as disclosed in the aforementioned U.S. Pat. Nos. 5,593,807 and 5,945,245, and wherein the resin selected preferably contains functional groups that render them dissipatable; that is, they form spontaneous emulsions in water without the use of organic solvents, especially above the glass transition temperature, Tg, of the resin. In other embodiments, the resin selected may require the use of organic solvents miscible with water, followed by emulsification process in water and then followed by stripping the solvent from water to form an aqueous resin dispersion. The latex of suspended resin particles may be comprised of particles which have an average size of from, for example, about 5 to about 500 nm and more preferably about 10 to about 250 nm in volume average diameter, as measured by any suitable device such as, for example, a NiCOMP® sizer. The particles preferably comprise, for example, about 5 to about 40 percent by weight of the latex emulsion.

The following Examples are being submitted to illustrate embodiments of the present disclosure. These Examples are intended to be illustrative only and are not intended to limit the scope of the present disclosure. Also, parts and percentages are by weight unless otherwise indicated.

EXAMPLES

The colorant-polyester polymer described below synthesized via a low temperature and controlled enzymatic polymerization was used to produce an emulsion aggregation toner composition. A portion of the colorant-polyester was emulsified with a crystalline resin using the phase inversion process to yield a stable emulsion of the colorant-polyester polymer. This emulsion was then used in an emulsion aggregation process as a replacement of the standard crystalline emulsion. The toner particles produced were within specification and fluorescent in color.

Example 1

Reaction Mechanisms for Producing Colorant-Polyester

An illustrative example of the enzymatic polymerization reaction is shown in Reaction Diagrams I and II. A colorant may be bound to an ester monomer through enzymatic polymerization method, creating a colorant-polyester polymer. The enzyme used may be Novozyne 435 (available from Novo Nordisk). (Reaction Diagram I)

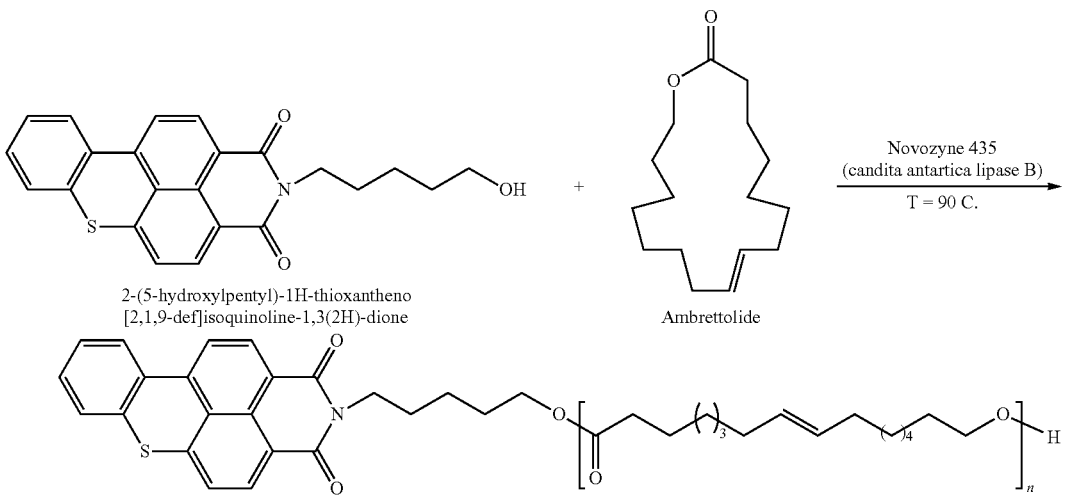

An ester monomer may also be polymerized through the enzymatic polymerization method initiated by water, optionally present in the reaction system, creating a polyester. (Reaction Diagram II)

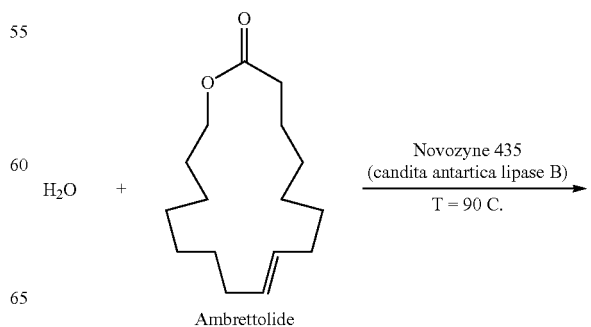

-continued

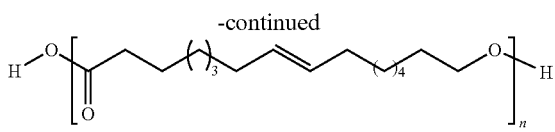

Example 2

Crystalline Polyester Latex Containing Florescent Colorant Prepared with Phase Inversion Emulsification Crystalline polyester resin (poly(nonylene-decanoate), 78 grams), fluorescent resin produced in U.S. patent application Ser. No. 12/879,587, filed Sep. 10, 2010 (22 grams), Methyl Ethyl Ketone (60 grams), and Isopropanol (10 grams) were weighted out and charged in a 1-liter glass Buchi reactor. The mixture was mixed at about 100 rpm with an anchor blade impeller and heated to about 76° C. to dissolve the resins in the solvent mixture. De-ionized water (DIW) (200 grams) was heated up to 96° C. on a hot plate. The resins began to melt/dissolve when the reactor temperature reached 71.5° C. The reactor temperature was set to 72° C. once the resin mixture dissolved. After a lapse of 27 minutes, a 10% $NH_3$ solution (5.4 grams) was added to the mixture drop-wise with a disposable pipette during a period of 2 minutes. The mixture was left to stir for 10 minutes. Pre-heated DIW (200 grams) was pumped into the reactor at a flow rate of 3.3 g/min over 60 minutes. The emulsion produced had a particle size of 193 nm as measured using a Nanotrac particle size analyzer. The mixture was poured into a glass pan, which was kept in the fume hood and stirred by a magnetic stir-bar to evaporate the solvent. The final latex obtained had a solid of 29.6%, a residual MEK/IPA of 5/30 ppm, and a pH of 7.68.

Example 3

EA Polyester Particle Made with a Polyester-Fluorescent Colorant

A polyester EA toner was prepared at the 2L Bench scale (165 grams dry theoretical toner). The two amorphous emulsions (127 grams of a 37 wt % poly(propoxylated bisphenol-A co-fumarate co-terephthalic acid co dedecenyl succinic anhydride) and 132 grams of a 35 wt % poly(propoxylated bisphenol-A co-ethoxylated bisphenol-A co-terephthalic acid co-dedecenyl succinic anhydride)), 54 grams crystalline emulsion with polyester-fluorescent dye (29.6% solids, 28.2% polyester-fluorescent dye content, 193 nm particle size), 4.4 grams surfactant (Dowfax), and 51 grams wax (IGI) are mixed, then pH adjusted to 4.2 using 0.3M nitric acid. The slurry is then homogenized for a total of 5 minutes at 3000-4000 rpm while adding in the coagulant, 2.96 grams aluminum sulphate mixed with 36.5 grams DI water. The slurry is then transferred to the 2L Buchi and set mixing at 460 rpm. The slurry is then aggregated at a batch temperature of 42° C. During aggregation, 131 grams of a shell latex containing the same amorphous emulsions as in the core was added and then the batch was held to achieve the targeted particle size. Once at the target particle size the aggregation step was frozen with pH adjustment using sodium hydroxide (NaOH) and 6.35 grams of chelating agent (Versene 100). The process proceeds with the reactor temperature (Tr) being increased to achieve 85° C., at the desired temperature the pH is adjusting to 7 using pH 5.7 sodium acetate/acetic acid buffer where the particles begin to coalesce. After about one hour particles achieve a circularity of >0.965 and are quench cooled. Final toner particle size, GSDv and GSDn were 5.83/1.18/1.19, respectively. The fines (1.3-3.2 microns), coarse (>16 microns) and circularity were 0.41%, 0.85% and 0.982.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A toner composition comprising:
   a colorant-polyester polymer comprising at least one colorant and at least one polyester resin,
   an optional non-colorant polyester,
   an optional additional colorant,
   an optional wax, and
   an optional additive,
   wherein
   the colorant in the colorant-polyester polymer is covalently linked to the polyester resin,
   the colorant is a fluorescent dye or fluorescent pigment excluding rhodamine,
   the colorant-polyester polymer is obtained from a reaction solution comprising the colorant, a lactone, and an enzyme catalyst, and
   the colorant-polyester polymer is included in the toner composition in an amount of from about 0.01 to about 15% by weight of the toner composition.

2. The toner composition of claim 1, wherein the colorant is covalently linked to the polyester resin at an α-position.

3. The toner composition of claim 1, wherein the fluorescent dye or fluorescent pigment is selected from the group consisting of carboxylic-indenofluorenone, 2-(5-hydroxyl-pentyl)-1H-thioxantheno[2,1,9-def]isoquinoline-1,3(2H)-dione, perylene, perinone, squaraine, β-oxynaphthoic acid pigment, 4,4'-bis(styryl)biphenyl, 2-(4-phenylstilben-4-yl)-6-butylbenzoxazole, 2-(2-hydroxyphenyl)benzothiazole, beta-methyl umbelliferone, 4,-methyl-7-dimethylaminocoumarin, 4-methyl-7-aminocoumarin, N-methyl-4-methoxy-1,8-naphthalimide, 9,10-bis(phenethynyl)anthracene, 5,12-bis (phenethynyl)naphthacene, 9,10-diphenyl anthracene, N-salicylidene-4-dimethylaminoaniline, 2-(2-hydroxyphenyl)benimidazole, 2-(2-hydroxyphenyl)benzoxazole, 1-[4-(2-hydroxyethoxy)-phenyl]-2-hydroxy-2-methyl-1-propane-1-one, and combinations thereof.

4. The toner composition of claim 1, wherein the lactone is one or more members selected from the group consisting of oxacycloheptadec-10-en-2-one, pentadecalactone, pentadecenlactone, hexadecenlactone, omega-pentadecalactone, caprolactone, propylmalolactonate, 2-methylene-4-oxa-12-dodecanolide, poly(butadiene-b-pentadecalactone, poly (butadiene-b-∈-CL), (R) and (S)-3-methyl-4-oxa-6-hexanolide, 3(S)-isopropylmorpholine-2,5-dione, Morpholine-2,5-dione derivatives, 1-methyl trimethylene carbonate, 8-octanolide, δ-Decalactone, 12-Dodecanolide, α-Methylene macrolides, and α-Methylene-δ-valerolactone.

5. The toner composition of claim 1, wherein the enzymatic catalyst is one or more members selected from the group consisting of lipase PA, lipase PC, lipase PF, lipase A, lipase CA, lipase B, lipase CC, lipase K, lipase MM, cutinase and porcine lipase.

6. The toner composition of claim 1, wherein the enzymatic catalyst is candita antarctica lipase B.

7. The toner composition of claim 1, wherein the toner composition is obtained by a process selected from the group consisting of an emulsion aggregation process, suspension process, chemical milling, and pulverization.

8. A powder coating composition comprising the toner composition of claim 1.

9. The toner composition of claim 1, wherein the colorant-polyester polymer has a $M_w$ from about 1,000 g/mol to about 50,000 g/mol, a $M_n$ from about 1,000 g/mol to about 50,000 g/mol, and a PDI of from about 1.00 to about 2.50.

10. A method for preparing a toner composition, the method comprising:
   forming a colorant-polyester resin emulsion comprising a colorant-polyester polymer and an optional non-colorant polyester,
   mixing the colorant-polyester resin emulsion, an optional colorant, an optional wax, and an optional additive to form a mixture, and
   aggregating and coalescing the mixture to form the toner composition,
   wherein
      the colorant-polyester polymer comprises at least one colorant and at least one polyester resin,
      the colorant is a fluorescent dye or fluorescent pigment excluding rhodamine,
      the colorant is covalently linked to the polyester resin,
      the colorant-polyester polymer is obtained from a reaction solution comprising the colorant, a lactone, and an enzyme catalyst, and
      the colorant-polyester polymer is included in the toner composition in an amount of from about 0.01 to about 15% by weight of the toner composition.

11. The method of claim 10, wherein the colorant is covalently linked to the polyester resin at an α-position.

12. The method of claim 10, wherein the fluorescent dye or fluorescent pigment is selected from the group consisting of carboxylic-indenofluorenone, 2-(5-hydroxylpentyl)-1H-thioxantheno[2,1,9-def]isoquinoline-1,3(2H)-dione, perylene, perinone, squaraine, β-oxynaphthoic acid pigment, 4,4'-bis(styryl)biphenyl, 2-(4-phenylstilben-4-yl)-6-butyl-benzoxazole, 2-(2-hydroxyphenyl)benzothiazole, beta-methyl umbelliferone, 4,-methyl-7-dimethylaminocoumarin, 4-methyl-7-aminocoumarin, N-methyl-4-methoxy-1,8-naphthalimide, 9,10-bis(phenethynyl)anthracene, 5,12-bis(phenethynyl)naphthacene, 9,10-diphenyl anthracene, N-salicylidene-4-dimethylaminoaniline, 2-(2-hydroxyphenyl)benimidazole, 2-(2-hydroxyphenyl)benzoxazole, 1-[4-(2-hydroxyethoxy)-phenyl]-2-hydroxy-2-methyl-1-propane-1-one, and combinations thereof.

13. The method of claim 10, wherein the lactone is one or more members selected from the group consisting of oxacyclohepadec-10-en-2-one, pentadecalactone, pentadecenlactone, hexadecenlactone, omega-pentadecalactone, caprolactone, propylmalolactonate, 2-methylene-4-oxa-12-dodecanolide, poly(butadiene-b-pentadecalactone, poly(butadiene-b-∈-CL), (R) and (S)-3-methyl-4-oxa-6-hexanolide, 3(S)-isopropylmorpholine-2,5-dione, Morpholine-2,5-dione derivatives, 1-methyl trimethylene carbonate, 8-octanolide, δ-Decalactone, 12-Dodecanolide, α-Methylene macrolides, and α-Methylene-δ-valerolactone.

14. The method of claim 10, wherein the enzymatic catalyst is one or more members selected from the group consisting of lipase PA, lipase PC, lipase PF, lipase A, lipase CA, lipase B, lipase CC, lipase K, lipase MM, cutinase and porcine lipase.

15. The method of claim 10, wherein the enzymatic catalyst is candita antarctica lipase B.

16. A method for preparing a toner composition, the method comprising:
   providing a reaction solution comprising an ester monomer, a colorant having or functionalized to have at least one hydroxyl group, and an enzymatic catalyst;
   reacting the ester monomer and the colorant using the enzymatic catalyst to produce a polymeric product, wherein the polymeric product comprises a colorant-polyester polymer;
   separating the polymeric product from the reaction solution;
   forming a latex from the polymeric product; and
   using the resulting polymeric product emulsion in an emulsion aggregation process to produce a toner composition,
   wherein
      the colorant-polyester polymer comprises at least one colorant and at least one polyester resin,
      the colorant is a fluorescent dye or fluorescent pigment excluding rhodamine,
      the colorant is covalently linked to the polyester resin,
      the polyester resin is obtained by polymerizing a lactone using an enzyme catalyst, and
      the colorant-polyester polymer is included in the toner composition in an amount of from about 0.01 to about 15% by weight of the toner composition.

17. The method of claim 16, wherein the emulsion aggregation process comprises:
   forming a colorant-polyester resin emulsion comprising the colorant-polyester polymer,
   mixing the colorant-polyester resin emulsion, an optional colorant, an optional wax, and an optional additive to form a mixture, and
   aggregating and coalescing the mixture to form the toner composition,
   wherein the colorant-polyester resin emulsion comprises a colorant covalently linked to some of the polyester resin, and the polyester resin is obtained by polymerizing a lactone using an enzyme catalyst.

* * * * *